United States Patent [19]
Jönsson et al.

[11] Patent Number: 5,833,949
[45] Date of Patent: Nov. 10, 1998

[54] METHOD FOR THE PREPARATION OF A MEDICAL SOLUTION

[75] Inventors: Lennart Jönsson, Furulund; Sven Jönsson, Staffanstorp, both of Sweden

[73] Assignee: Gambro AB, Sweden

[21] Appl. No.: 132,765

[22] Filed: Oct. 6, 1993

Related U.S. Application Data

[63] Continuation of Ser. No. 776,561, Oct. 15, 1991, abandoned.

[30] Foreign Application Priority Data

Oct. 15, 1990 [SE] Sweden .................................. 9003278

[51] Int. Cl.$^6$ .............................. A61L 9/04; A61K 31/19; A01N 37/00
[52] U.S. Cl. .............................................. 424/44; 514/574
[58] Field of Search ................................ 424/44; 514/574

[56] References Cited

U.S. PATENT DOCUMENTS

| | | | |
|---|---|---|---|
| 4,161,458 | 7/1979 | Kolleth | 252/305 |
| 4,668,400 | 5/1987 | Veech . | |
| 4,784,495 | 11/1988 | Jonsson et al. . | |
| 4,929,449 | 5/1990 | Veech | 424/700 |
| 5,032,615 | 7/1991 | Ward et al. | 514/574 |
| 5,091,094 | 2/1992 | Veech | 210/647 |

FOREIGN PATENT DOCUMENTS

| | | |
|---|---|---|
| 0209607 | 5/1985 | European Pat. Off. . |
| 3844174 A1 | 7/1990 | Germany . |

OTHER PUBLICATIONS

Klein, et al., "Calcium Carbonate Precipitation in Bicarbonate Hemodialysis," Thoughts and Progress, Artif Organs, vol. 10, No. 3, 1986, pp. 248–250.

Ing. et al., "Bicarbonate–buffered peritoneal dialysis," The International Journal of Artificial Organs, vol. 8, No. 3, 1985, pp. 121–124.

Organikum textboook, Berlin 1971, pp. 149–150.

Patent Abstract of Japan, vol. 6, n. 49 (CO96) Mar. 31, 1982; publication No. JP56164113, Dec. 17, 1981, Minoru et al., "Preparation of Dialysis Solution".

Merck Index 10th Ed, 1984, # 8414.

Merck Index 10th Ed # 1793.

Veech 113:CA:158753j 1990.

*Primary Examiner*—Marianne M. Cintins
*Attorney, Agent, or Firm*—Lerner, David, Littenberg, Krumholz & Mentlik

[57] ABSTRACT

A method for preparation of a medical solution from water and a plurality of concentrates, including at least one acid in gaseous form, comprises the steps of transporting the water from a source through a main conduit and successively adding the plurality of concentrates to the water in the main conduit at a plurality of predetermined points positioned along the main conduit.

17 Claims, 1 Drawing Sheet

METHOD FOR THE PREPARATION OF A MEDICAL SOLUTION

This is a continuation of application Ser. No. 07/776,561 filed Oct. 15, 1991, now abandoned.

This invention relates generally to a method and apparatus for the preparation of a medical solution. More particularly, this invention relates to a method and apparatus for preparing a dialysis solution from a liquid such as water and a plurality of concentrates, and carbon dioxide in gaseous form, whereby respective concentrates are supplied successively to a number of predetermined points along a main conduit which leads from a water source to a dialyzer. Still more particularly, the present invention relates to a method and a system for preparing a dialysis solution from water and a plurality of concentrates including an acid in gaseous form and bicarbonate as a buffer.

BACKGROUND OF THE INVENTION

Methods for the preparation of dialysis solutions using bicarbonate as the buffer are generally disclosed in the prior art. This is shown, for example, in European Patent B1-0 022 922. Likewise, a system for the preparation of a medical solution, preferably intended for dialysis, is also known in the art and is disclosed in U.S. Pat. No. 4,784,495.

In U.S. Pat. No. 4,784,495, a system for preparing a medical solution from water and at least one concentrate in powder form is disclosed. The system disclosed therein includes a water source, a powder source, and at least one liquid concentrate source.

In European Pat. B1-0 022 922 a method for the preparation of a medical solution is disclosed in which two liquid concentrates are used. U.S. Pat. No. '495 teaches a substantial improvement over the European Patent '922 by disclosing a system which replaces one of the liquid concentrates with a concentrate in powder form, thereby removing some of the disadvantages associated with the use of concentrates in liquid form. However, a certain quantity of liquid concentrate must still be used in the system disclosed in U.S. Pat. No. '495, which results in various disadvantages.

The present invention discloses an improved method and system for preparation of a medical solution from water and a plurality of concentrates, wherein carbon dioxide is added in gaseous form. The use of the gaseous carbon dioxide with the concentrates makes it possible to use concentrates in powder form for the remaining required concentrates if desired. The only liquid which is absolutely required is water.

Thus, the present invention improves upon the prior art by eliminating problems associated with transporting large quantities of liquid over long distances and reducing the bacteria growth, which is normally considerably less in a powder form concentrate than in a concentrate in liquid form.

SUMMARY OF THE INVENTION

The present invention relates to a method of preparing a dialysis solution which comprises the steps of transporting water through a main conduit while successively adding a first concentrate, carbon dioxide in a gaseous form, and a second concentrate, to the water at a plurality of predetermined points along the main conduit. As used herein, the term "carbon dioxide" refers to the same material which was previously referred to herein as carbon dioxide constituting a "concentrate".

The present invention also pertains to an apparatus for preparing a dialysis solution from water and a plurality of concentrates and gaseous carbon dioxide, the apparatus comprising a water source, a main conduit for transporting the water through the apparatus, and a plurality of concentrate sources for supplying the plurality of concentrates to the water in the main conduit at a plurality of predetermined points, including at least one gas inlet, along the main conduit.

Preferably the invention is intended to be used in connection with a method applied to a dialysis system which uses sodium bicarbonate as the buffer and to which calcium is also supplied. In such a case, the addition of the carbon dioxide in gas form ought to occur before these substances are blended. In this way the risk of precipitation of solid calcium carbonate is reduced.

Surplus gas which is supplied, if any, can be removed in connection with normal degassing. Thereafter this can possibly be recirculated. This can be desirable, partially from an economic point of view and partially for facilitating the control of the finally supplied quantity of gas.

The control of the supplied quantity of gas can also be facilitated by measuring the pH-value of the prepared solution after the addition of gas and using this for its regulation.

Considerable advantages, such as from a transportation point of view, are gained if the gas is prepared in situ. If this concerns a dialysis system which uses sodium bicarbonate as the buffer, then it is suitable that $CO_2$ is chosen as such a gas. This can be prepared in situ by mixing a carbonate, preferably sodium bicarbonate, with acid and water. A suitable acid for the preparation is citric acid.

Alternative, $CO_2$ can be prepared in situ by heating a carbonate, preferably sodium bicarbonate, to a suitable temperature, such as above 50° C. From a hygienic view point, it can be appropriate that water formed during the preparation is separated off before the supply to the main line.

The invention thus relates also to a system for continuous preparation of a medical solution, for example a dialysis solution from water and a plurality of concentrates, whereby respective concentrates are arranged to be supplied successively to a number of predetermined points along a main conduit which leads from a water source to a point of consumption, such as a dialyzer. The system is characterized in that one of said dosage points constitutes a gas inlet for the intake of said carbon dioxide in gas form.

The invention is preferably intended to be applied to a system adapted for use for dialysis with sodium bicarbonate as the buffer and to which calcium is also supplied. In such a case, the predetermined inlet point for the carbon dioxide in gas form should be positioned between the dosage points for these substances.

The system preferably includes means for measuring the pH-value after the addition of gas. Other measuring devices can however also be used, such as a conductivity meter.

Considerable advantages are attained if the system includes means for preparation of the $CO_2$ in gas form in situ. Other gases can however also be used, such as hydrochloric acid in gas form.

Accordingly, it is an object of the present invention to provide an improved method of preparing a dialysis solution from water and a plurality of concentrates, and carbon dioxide where the carbon dioxide is supplied in gaseous form.

It is another object of the present invention to provide an improved method for preparing a dialysis solution where at least one of the plurality of concentrates is in powder form.

It is another object of the present invention to provide an improved method for preparing a dialysis solution in which liquid concentrates can be totally avoided.

It is still another method of the present invention to provide an improved method for preparing a dialysis solution where the gaseous carbon dioxide is prepared in situ.

It is still another object of the present invention to provide an improved method for preparing a dialysis solution which will eliminate or at least greatly diminish problems inherent in the prior art methods such as complications associated with transporting large quantities of liquid over long distances and the problem of bacteria growth in liquid concentrates.

It is still another object of the present invention to provide an improved method for preparing a dialysis solution in which a concentrate can be supplied in the form of a pure acid to eliminate the need of adding metal salts in conjunction with the acid, as prior art methods require.

It is still another object of the present invention to provide an improved apparatus for preparing a dialysis solution from water and a plurality of concentrates in which carbon dioxide in gaseous form can be prepared or supplied and transported to a main conduit to become part of the dialysis solution.

These and other objects of the present invention will be more clearly understood when read in conjunction with the detailed description and the accompanying drawings which follow.

DETAILED DESCRIPTION

Figure 1:
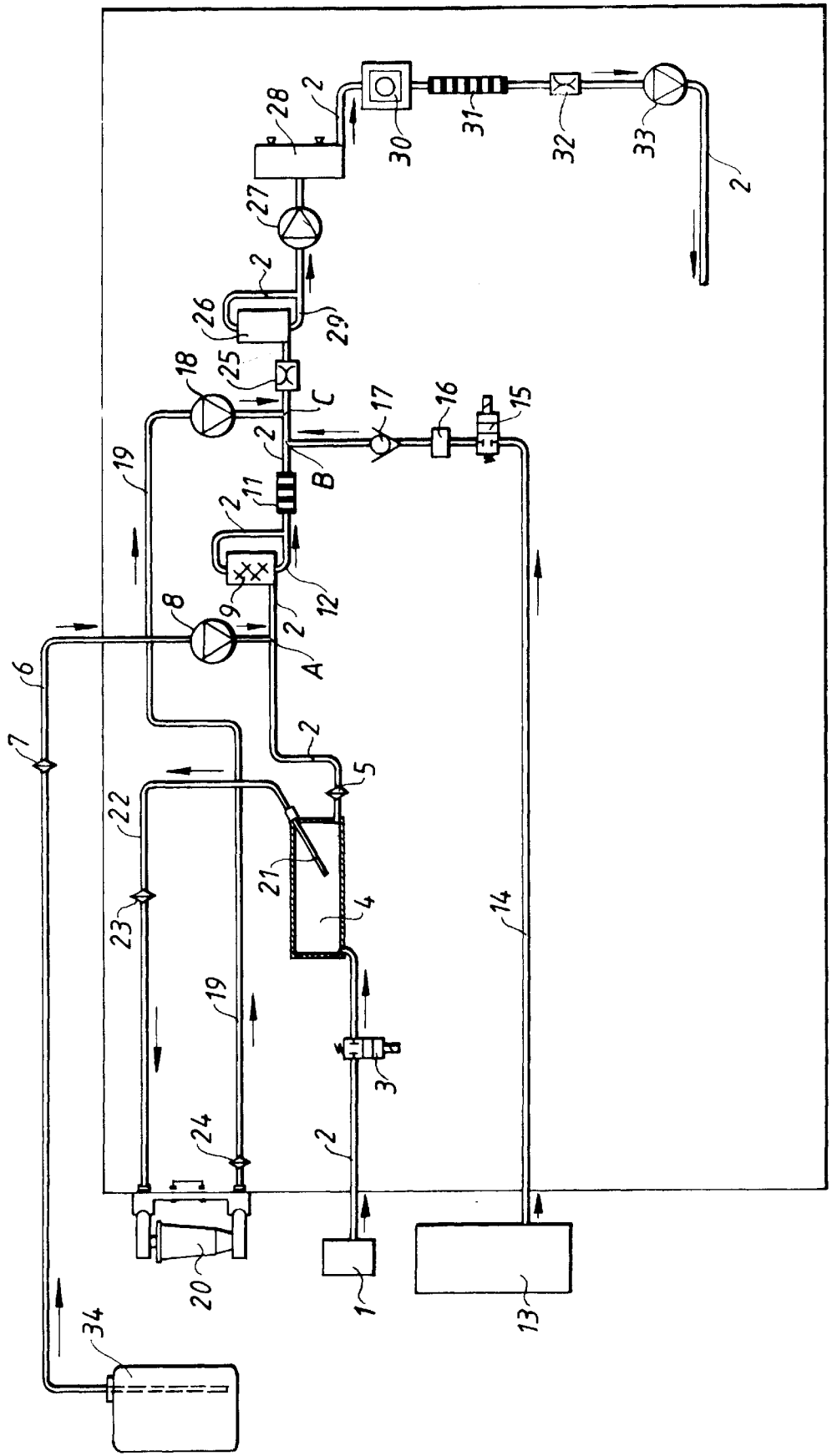
FIG. 1 is a block diagram of a system or a plant for preparation of a medical solution, preferably a dialysis solution in accordance with a preferred form of the present invention.

Referring to the drawings, FIG. 1 shows a preferred form of the apparatus for preparation of a medical solution in accordance with the present invention.

In the preferred embodiment shown, water is supplied from a source 1, for example a reverse-osmosis unit. Alternatively, the source 1 can constitute a hospital's central system in which water has already been supplied with one or more concentrates in fixed concentrations. In the following, the expression water source is meant not solely a source for pure water, but also sources for water to which one or more substances have been added. The water is fed via a main conduit 2 with a valve 3 to a heating vessel 4, where it is heated to a temperature, for example circa 37° C. The main conduit 2 then continues via a filter 5 to a mixing point A. A liquid-based concentrate is supplied from a reservoir 34 via a conduit 6 with a filter 7. Alternatively, this concentrate can be supplied in powder form and dissolved in situ by water from the water source 1 being fed therethrough, as is described, for example, in the above-mentioned U.S. Pat. No. 4,784,495 or in the Swedish Patent Application 90.00586-9. The concentrate from the source 34 or concentrate prepared in the above-mentioned way is supplied to the main conduit 2 with the aid of a pump 8.

In order to achieve good mixing, the water and concentrate are fed to a mixing vessel 9 and from there to a conductivity meter 11. So that the mixing vessel 9 can be emptied after treatment has been carried out, it is provided with a separate drainage conduit 12 at its base. The conductivity meter 11 is appropriately arranged to control the pump 8 in order to achieve the correct mixing ratio between water and concentrate.

According to the invention, carbon dioxide is supplied to the main conduit 2 in the form of a gas. This gas is drawn from a reservoir 13 therefor. This reservoir can either consist of a gas bottle with suitable gas, for example carbon dioxide or HCl in gas form. Alternatively, it can consist of a device for preparing the gas in situ. By way of example, $CO_2$ can be prepared in situ by means of a carbonate, preferably sodium bicarbonate, being mixed with acid and water. An example of a suitable acid for this purpose is citric acid. Alternatively, $CO_2$ can be prepared by warming a carbonate, preferably sodium bicarbonate, to a suitable temperature, such as over 50° C.

The gas from the reservoir 13 is then led through a conduit 14, a valve 15, a flow regulation valve 16 and a non-return valve 17 to a mixing point B in the main conduit 2.

A second concentrate from a reservoir 20 in the form of a powder cartridge is then supplied to a point C in the main conduit with the aid of a pump 18 via conduit 19. The powder therein is dissolved continuously by water being drawn from the heating vessel via a tube 21 and a conduit 22 with a filter 23. The conduit 19 also includes a filter 24. The dissolving of the powder in the cartridge 20 can occur in a way as described in the above-mentioned U.S. Pat. No. '495.

The prepared liquid is delivered from the mixing point C via a throttle 25 and bubble chamber 26 with the aid of a pump 27 to a bubble trap 28. Through this arrangement, bubbles are formed from mainly air dissolved in the liquid and any surplus gas supplied from the reservoir 13. These bubbles are enlarged in the bubble chamber 26 and removed in the bubble trap 28 in a not shown way. These together with a smaller quantity of liquid, can possibly be led directly to a drain or may also be recirculated so that surplus gas can also be dissolved. Like the mixing vessel 9, the bubble chamber 26 is also provided with a drainage conduit 29 at its base. Thus, this can be completely emptied when the system for example is to be cleaned.

The main conduit 2 extends from the bubble trap 28 via a pH-meter 30, a conductivity meter 31, a throttle 32 and a pump 33 to a not shown dialyzer. The pH-meter 30 is hereby suitably arranged to control the flow regulator 16 in the conduit 14. The conductivity meter 31 is further suitably arranged to control the pump 18 in the conduit 19. These pumps can alternatively consist of some type of adjustable dosage pump to which a suitable value can be inputted in relation to the flow of liquid through the main conduit 2.

The components 32 and 33 can be parts of a constant flow device of the type which is described in more detail in U.S. Pat. No. 4,762,618. In such a case, a pressure meter is provided therebetween which controls the pump 33 so that a constant pressure drop is maintained across the throttle 32 and thereby a constant flow to the dialyzer.

EXAMPLE FOR PREPARATION OF $CO_2$

1. Sodium bicarbonate mixed with acid and water

Acid in dry form, such as citric acid, is mixed in suitable quantities with sodium bicarbonate. For dialysis treatment the suitable quantities are circa 37 g citric acid and 45 g sodium bicarbonate. When water is added, the formation of $CO_2$ commences. In order to moderate the supply of gas, either the water supply to the powder mixture can be regulated and thereby control the gas production, or the gas can be allowed to be collected in a reservoir under pressure and the supply of gas to the main conduit can be regulated with a flow regulating device.

2. Sodium bicarbonate heated to conversion temperature

Dry sodium bicarbonate is heated to a temperature above 50° C. in a gas-tight vessel which is connected to the point of consumption. The gas production is directly proportional to this supply of energy. In this way, the gas production can be controlled as needed. In order to control the quantity of supplied energy, either the gas flow or the pH-value in the ready dialysis liquid can be measured.

DETAIL INFORMATION

Surplus gas can either be separated off in connection with the normal degassifying or can be brought to recirculate in the system.

Parameters which effect the quantity of supplied acid are, amongst others, the pressure at the dosage intake point, the temperature of the liquid, exposure time for the gas (contact distance/flow velocity) and contact surface (total bubble surface).

Other gases such as hydrochloric acid in gas form can be used in the preparation of the dialysis solution. The hydrochloric acid need not be in gas form from the outset. Instead this can be generated in situ by mixing for example sodium chloride with suitable acid, such as sulfuric acid, during heating. However, it is preferable to use $CO_2$. Furthermore, it should be noted that the conductivity meter 31 can be arranged solely for control of the preparation. In such case, the flow control valve 16 can totally control the gas flow in the conduit 14. Besides regulating means, in such a case this can also include means for measuring the flow. Furthermore, the parts included in the described system can be carried within wide limits concerning both form and function.

While the foregoing description and figures are directed to the preferred embodiment of the method and system for preparation of a dialysis solution in accordance with the present invention, it should be appreciated that certain modifications can be made, and are, indeed, encouraged to be made, in the materials, structure and arrangement of the disclosed embodiment without departing from the spirit and scope of the present invention which is intended to be captured by the claims set forth below.

We claim:

1. A method of continuously preparing a dialysis solution for its direct in-line use in a dialyzer comprising the steps of:
    a. transporting water from a source, through a main conduit from which said dialysis solution is to be directly supplied to said dialyzer;
    b. providing $CO_2$ in gaseous form;
    c. successively adding a first concentrate, said $CO_2$ in gaseous form, and a second concentrate to said water in said main conduit at a plurality of predetermined points along said main conduit including a first predetermined point, a second predetermined point disposed downstream of said first predetermined point, and a third predetermined point disposed downstream of said second predetermined point, one of said first and second concentrates comprising bicarbonate, said first concentrate being added to said main conduit at said first predetermined point, said $CO_2$ in its gaseous state being added to said main conduit at said second predetermined point, and said second concentrate being added to said main conduit at said third predetermined point, whereby the precipitation of carbonates is minimized and said dialysis solution including said plurality of concentrates is continuously provided to said dialyzer therefrom.

2. A method as claimed in claim 1 wherein said first concentrate comprises said sodium bicarbonate.

3. The method as claimed in claim 2 wherein said first concentrate includes calcium.

4. A method as claimed in claim 1 wherein said second concentrate comprises sodium bicarbonate.

5. The method as claimed in claim 4 wherein said first concentrate comprises calcium.

6. A method of preparing a medical solution comprising the steps of:
    a. transporting a liquid comprising water from a source, through a main conduit from which said medical solution is to be supplied;
    b. providing $CO_2$ in gaseous form; and
    c. successively adding a first concentrate, said $CO_2$ in gaseous form, and a second concentrate to said liquid in said main conduit at a plurality of predetermined points along said main conduit including a first predetermined point, a second predetermined point disposed downstream of said first predetermined point, and a third predetermined point disposed downstream of said second predetermined point, one of said first and second concentrates comprising bicarbonate, said first concentrate being added to said main conduit at said first predetermined point, said $CO_2$ in the gaseous state being added to said main conduit at said second predetermined point, and said second concentrate being added to said main conduit at said third predetermined point, whereby the precipitation of carbonates is minimized, and a medical solution including said plurality of concentrates is provided.

7. A method as claimed in claim 6 wherein the other of said first and second concentrates comprises calcium.

8. A method as claimed in claim 6 further comprising the step of removing surplus gas in said medical solution downstream of said third predetermined point.

9. A method as claimed in claim 8 further comprising the step of reblending said surplus gas removed from said medical solution with said water and said plurality of concentrates.

10. A method as claimed in claim 8 further comprising the step of measuring the pH value of said medical solution downstream of said third predetermined point.

11. A method as claimed in claim 10 including the step of controlling said addition of said $CO_2$ to said water based upon said measured value of said pH.

12. A method as claimed in claim 6 wherein said second concentrate is a buffer comprising sodium bicarbonate.

13. A method as claimed in claim 12 wherein said first concentrate comprises calcium.

14. A method as claimed in claim 6 wherein said first concentrate is a buffer comprising sodium bicarbonate.

15. A method as claimed in claim 14 wherein said second concentrate comprises calcium.

16. A method of continuously preparing a dialysis solution for its direct in-line use in a dialyzer comprising the steps of:
    a. transporting an aqueous liquid from a source, through a main conduit from which said dialysis solution is to be directly supplied to said dialyzer;
    b. adding a first concentrate comprising bicarbonate to said aqueous liquid at a first point along said main conduit;
    c. adding gaseous $CO_2$ to said aqueous liquid at a second point along said main conduit downstream from said first point; and
    d. adding a second concentrate comprising calcium to said aqueous liquid at a third point along said main conduit downstream from said second point;
    whereby the precipitation of carbonates is minimized and said dialysis solution including said concentrates is continuously provided to said dialyzer from said main conduit.

17. A method of continuously preparing a dialysis solution for its direct in-line use in a dialyzer comprising the steps of:

a. transporting an aqueous liquid from a source, through a main conduit from which said dialysis solution is to be directly supplied to said dialyzer;

b. adding a first concentrate comprising calcium to said aqueous liquid at a first point along said main conduit;

c. adding gaseous $CO_2$ to said aqueous liquid at a second point along said main conduit downstream from said first point; and d. adding a second concentrate comprising bicarbonate to said aqueous liquid at a third point along said main conduit downstream from said second point;

whereby the precipitation of carbonates is minimized and said dialysis solution including said concentrates is continuously provided to said dialyzer from said main conduit.

* * * * *

UNITED STATES PATENT AND TRADEMARK OFFICE
CERTIFICATE OF CORRECTION

PATENT NO. : 5,833,949
DATED : November 10, 1998
INVENTOR(S) : Jönsson et al.

It is certified that error appears in the above-identified patent and that said Letters Patent is hereby corrected as shown below:

Column 5, line 66, "first" should read --second--.

Signed and Sealed this

Twenty-third Day of February, 1999

Attest:

Q. TODD DICKINSON

*Attesting Officer*        *Acting Commissioner of Patents and Trademarks*